(12) United States Patent
Jugl et al.

(10) Patent No.: US 10,130,778 B2
(45) Date of Patent: Nov. 20, 2018

(54) CAP FOR A DRUG DELIVERY DEVICE AND DRUG DELIVERY DEVICE

(71) Applicant: Sanofi-Aventis Deutschland GmbH, Frankfurt am Main (DE)

(72) Inventors: Michael Jugl, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 363 days.

(21) Appl. No.: 14/421,356

(22) PCT Filed: Aug. 15, 2013

(86) PCT No.: PCT/EP2013/067056
§ 371 (c)(1),
(2) Date: Feb. 12, 2015

(87) PCT Pub. No.: WO2014/029679
PCT Pub. Date: Feb. 27, 2014

(65) Prior Publication Data
US 2015/0231339 A1 Aug. 20, 2015

(30) Foreign Application Priority Data
Aug. 20, 2012 (EP) .................................... 12180957

(51) Int. Cl.
*A61M 5/50* (2006.01)
(52) U.S. Cl.
CPC ..... *A61M 5/5086* (2013.01); *A61M 2205/583* (2013.01)

(58) Field of Classification Search
CPC ............................................. A61M 2005/3104
(Continued)

(56) References Cited

U.S. PATENT DOCUMENTS 533,575 A 2/1895 Wilkens
4,759,651 A 7/1988 Manusch et al.
(Continued)

FOREIGN PATENT DOCUMENTS

DE 3441435 A1 8/1985
DE 102010061061 A1 6/2012
(Continued)

OTHER PUBLICATIONS

Communication Pursuant to Article 94(3) EPC issued in European Patent Application No. 13753835.1 dated Apr. 8, 2016.
(Continued)

*Primary Examiner* — Amber Stiles
(74) *Attorney, Agent, or Firm* — Fish & Richardson P.C.

(57) ABSTRACT

A cap for a drug delivery device is provided, the cap comprising a main body and at least one indication element which is moveably retained in the main body, wherein the indication element is configured to be moved from a first position to a second position with respect to the main body, and wherein an information indicated to a user by the cap is changed when the indication element is moved from the first position into the second position. Furthermore, a drug delivery device comprising the previously described cap and an interaction member is provided.

13 Claims, 2 Drawing Sheets

(58) Field of Classification Search
USPC .................... 604/111, 192, 198, 263, 240
See application file for complete search history.

(56) References Cited

U.S. PATENT DOCUMENTS

| | | | |
|---|---|---|---|
| 5,226,895 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,203 | A | 10/1997 | Lewandowski |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,585,691 | B1 | 7/2003 | Vitello |
| 6,899,698 | B2 | 5/2005 | Sams |
| 6,936,032 | B1 | 8/2005 | Bush, Jr. et al. |
| 7,241,278 | B2 | 7/2007 | Moller |
| 7,815,611 | B2 | 10/2010 | Giambattista et al. |
| 2002/0004648 | A1* | 1/2002 | Larsen .................. A61M 5/326 604/195 |
| 2002/0052578 | A1 | 5/2002 | Moller |
| 2002/0120235 | A1 | 8/2002 | Enggaard |
| 2002/0133122 | A1* | 9/2002 | Giambattista ....... A61M 5/3202 604/198 |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0004532 | A1* | 1/2005 | Woehr .................. A61M 5/158 604/263 |
| 2005/0096597 | A1* | 5/2005 | Crawford .............. A61M 5/326 604/198 |
| 2005/0113765 | A1 | 5/2005 | Veasey et al. |
| 2005/0148933 | A1* | 7/2005 | Raven .................. A61M 5/002 604/111 |
| 2006/0153693 | A1 | 7/2006 | Fiechter et al. |
| 2009/0227956 | A1* | 9/2009 | Emmott ................ A61M 5/002 604/196 |
| 2009/0275916 | A1 | 11/2009 | Harms et al. |
| 2013/0237911 | A1 | 9/2013 | Von Schuckmann |

FOREIGN PATENT DOCUMENTS

| | | | |
|---|---|---|---|
| EP | 0220487 A1 | 5/1987 | |
| EP | 0937471 | 8/1999 | |
| EP | 0937476 | 8/1999 | |
| GB | 2142612 A | 1/1985 | |
| JP | H05-337182 A | 12/1993 | |
| JP | 2004-504891 A | 2/2004 | |
| WO | 99/38554 | 8/1999 | |
| WO | 01/10484 | 2/2001 | |
| WO | 2008058666 A1 | 5/2008 | |
| WO | 2008058668 A1 | 5/2008 | |
| WO | 2011/078851 A1 | 6/2011 | |
| WO | WO 2011078851 A1 * | 6/2011 | ............ A61M 5/326 |
| WO | 2011092518 A2 | 8/2011 | |
| WO | WO 2012076388 A1 * | 6/2012 | .......... A61M 5/5086 |

OTHER PUBLICATIONS

English Translation of First Office Action issued in Chinese Patent Application No. 201380043333.6 dated Sep. 28, 2016.
English Translation of Notice of Reasons for Rejection issued in Japanese Patent Application No. 2015-527861 dated Apr. 18, 2017.
English Translation of Decision of Rejection issued in Japanese Patent Application No. 2015-527861 dated Aug. 29, 2017.

* cited by examiner

CAP FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2013/067056 filed Aug. 15, 2013, which claims priority to European Patent Application No. 12180957.8 filed Aug. 20, 2012. The entire disclosure contents of these applications are herewith incorporated by reference into the present application.

FIELD OF INVENTION

This disclosure relates to a cap for a drug delivery device and drug delivery device comprising the cap.

BACKGROUND

In a drug delivery device, often, a cap is provided for covering at least parts of the device. In this way, internal components of the device can be prevented from environmental influences.

A drug delivery device is described in documents WO 2008/058666 A1 and WO 2008/058668 A1, for example.

SUMMARY

It is an object of the present disclosure to provide an improved cap. Furthermore, it is an object of the present disclosure to provide an improved drug delivery device.

This object may, inter alia, be achieved by the subject matter of the independent claim. Advantageous embodiments and refinements are the subject matter of the dependent claims. However, further advantageous concepts may be disclosed herein besides the ones which are currently claimed.

One aspect relates to a cap for a drug delivery device. The cap may be adapted and arranged to cover a dispensing end of the device. The cap may comprise a main body. Furthermore, the cap may comprise at least one indication element. The cap may comprise two or more indication elements. The indication element may be moveably retained, preferably permanently retained, in the cap, in particular in the main body. The indication element may be retained inside the cap, in particular inside the main body. The indication element may be configured to be moved from a first position to a second position with respect to the main body. The cap may be configured to provide an information to a user. The information may indicate the state of use of the device. The information may indicate whether the cap was removed from the device at least once and, particularly, whether the cap was removed for the first time after the cap was connected to an element of the device. Accordingly, the term that the information indicates a state of use, does not necessarily mean that the information indicates whether a dose of drug has been dispensed from the device. Rather, the information may indicate whether the user has removed the cap at least once and, thus, has reduced the sterility of the device as supplied by the manufacturer. By means of the information, the user may be able to distinguish between a new device and a device which is in use, e.g. a device from which the cap was removed at least once. The information indicated to the user by the cap may be changed when the indication element is moved from the first position into the second position.

When the indication element is positioned in the first position, the indication element may be prevented from being viewed by the user, e.g. by means of the main body. In other words, the indication element may be hidden by the main body. Accordingly, the main body may be non-transparent. When the indication element is prevented from being viewed by the user, the user may know that the device has not been used yet and/or that the cap has not yet been removed from the device for the first time.

When the indication element is positioned in the second position, the indication element may be visible to the user, e.g. through a window provided in the main body of the cap. Accordingly, when the indication element is moved from the first position into the second position, the indication element may become visible to the user. When the user sees the indication element, he may know at once that the device is in use or has been used at least once and/or that the cap has been removed from the device at least once. Whichever position the indication element may have, the user can realize at once the state of use of the device when looking at the cap. This may help to increase user safety.

A further aspect relates to a drug delivery device. The drug delivery device may comprise the previously described cap. Accordingly, features which are described herein above and below for the cap may also apply to the device and vice versa.

The device may further comprise an interaction member. The interaction member may be adapted and arranged to interact with the indication element. The indication element may be moved from the first position to the second position when the interaction member mechanically cooperates with the indication element. The indication element may be moved from the first position into the second position only when the cap is removed from the device, in particular when the cap is removed from the device for the first time.

The interaction member may be part of a component of the device. When the cap is moved with respect to the device, e.g. when the cap is removed from the device, the interaction member may mechanically cooperate with the indication element. In this way, the information provided by the cap may change when the interaction member mechanically cooperates with the indication element. The user may know at once by viewing the cap whether the device is in use or not, in particular whether the cap has been removed at least once or not. This may help to increase user safety.

According to a preferred embodiment, a cap for a drug delivery device is provided comprising a main body and at least one indication element which is moveably retained in the main body. The indication element is configured to be moved from a first position to a second position with respect to the main body, wherein an information indicated to a user by the cap is changed when the indication element is moved from the first position into the second position.

According to a preferred embodiment, a drug delivery device comprising the previously described cap and an interaction member is provided, the interaction member being adapted and arranged to interact with the indication element such that the indication element is moved from the first position to the second position when the interaction member mechanically cooperates with the indication element.

Of course, features described above in connection with different aspects and embodiments may be combined with each other and with features described below.

BRIEF DESCRIPTION OF THE DRAWINGS

Further features and refinements become apparent from the following description of the exemplary embodiments in connection with the accompanying figures.

DETAILED DESCRIPTION

Figure 1:
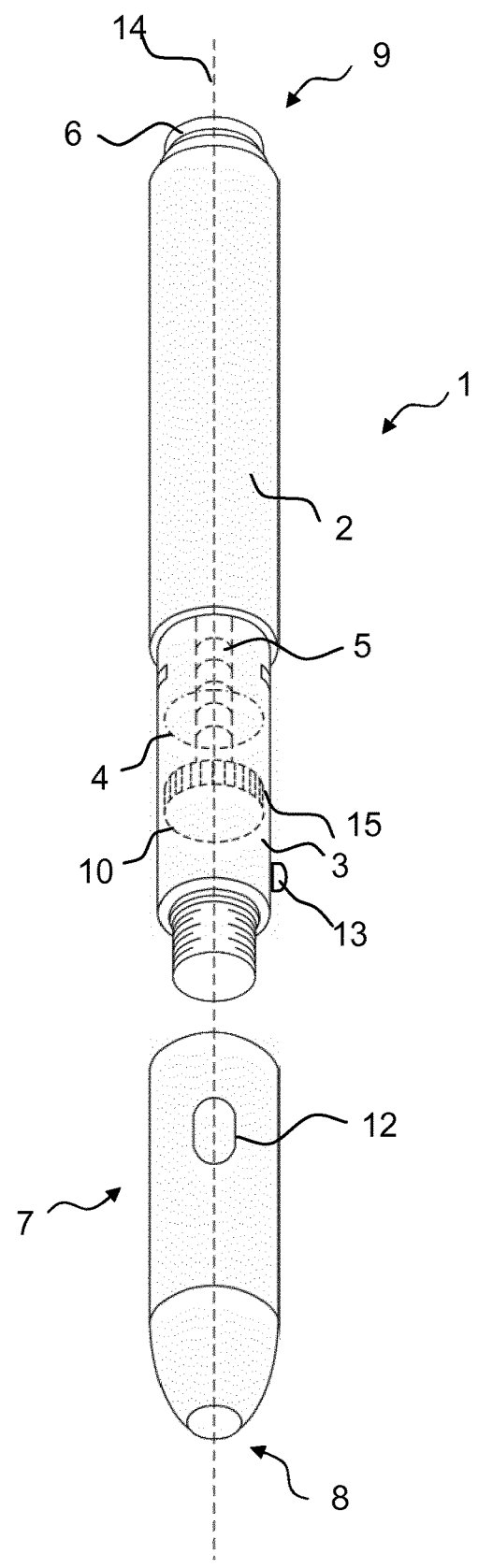
FIG. 1 schematically shows a perspective side view of a drug delivery device.

Like elements, elements of the same kind and identically acting elements may be provided with the same reference numerals in the figures.

In FIG. 1 a drug delivery device 1 shown. The drug delivery device 1 comprises a housing 2. The drug delivery device 1 and/or a component thereof have a distal end and a proximal end. The distal end is indicated by arrow 8. The proximal end is indicated by arrow 9. The term "distal end" designates that end of the drug delivery device 1 or a component thereof which is or is to be arranged closest to a dispensing end of the drug delivery device 1. The term "proximal end" designates that end of the system 1 or a component thereof which is or is to be arranged furthest away from the dispensing end of the system 1. The distal end and the proximal end are spaced apart from one another in the direction of an axis 14. The axis may be the longitudinal axis of the drug delivery device 1 or elements thereof.

The drug delivery device 1 comprises a drug retainer 3, 4. The drug retainer 3, 4 may comprise a cartridge holder 3. The drug delivery device 1 comprises a cartridge 4. The cartridge 4 is retained within the cartridge holder 3. The cartridge holder 3 stabilizes the position of the cartridge 4 mechanically. In an alternative embodiment, the drug retainer 3, 4 may comprise the cartridge 4. In this embodiment, the cartridge holder 3 may be redundant.

The cartridge holder 3 in particular the proximal end of the cartridge holder 3 is connectable, e.g. by a threaded engagement, to the housing 2 of the drug delivery device 1. Alternatively, in the embodiment where the cartridge holder 3 is redundant, the cartridge 4 may be directly connected to the housing 2 (see, for example, FIG. 1).

The cartridge 4 contains a drug 10, preferably a plurality of doses of the drug 10. The drug 10 may be a liquid drug.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDahttp://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A bung 15 is moveably retained within the cartridge 4. The bung 15 seals the cartridge 4 proximally. Particularly, the cartridge 4 may be a, e.g. pre-filled, cartridge. Movement of the bung 15 in the distal direction with respect to the cartridge 4 causes the drug 10 to be dispensed from the cartridge 4, provided that fluid communication between the distal end of the cartridge 4 and the environment, e.g. via a needle (not explicitly shown in the Figures), is established.

The drug delivery device 1 may be a pen-type device, in particular a pen-type injector. The device 1 may be configured for dispensing fixed doses of the drug 10, i.e. doses which may not be varied by a user. Alternatively, the device 1 may be configured to dispensing variable doses of the drug 10, i.e. doses which can be varied by the user. The device 1 can be a re-usable device, which means that the cartridge 4 can be replaced, in particular during a reset operation, by a replacement reservoir for dispensing a plurality of doses from the replacement reservoir. Alternatively, the device 1 may be a disposable device. In this case, the cartridge 4 may not be replaced. The cartridge 4 may, for example, be non-releasably connected to the cartridge holder 3. The drug delivery device 1 may be a multidose device, i.e. a device configured for setting and dispensing a plurality of doses of the drug 10. The drug delivery device 1 comprises a drive mechanism. The drive mechanism 10 may be retained in the housing 2. The drive mechanism is used for setting and dispensing a dose of the drug 10.

The drive mechanism comprises a piston rod 5. The piston rod 5 has a distal and a proximal end. The distal end of the piston rod 5 may be the end which is closest to the distal end of the drug delivery device 1 when the piston rod 5 has been introduced in the device 1. The proximal end of the piston rod 5 may be the end which is furthest away from the distal end of the drug delivery device 1 when the piston rod 5 has been introduced in the device 1. The piston rod 5 extends through the housing 2 of the device 1. The piston rod 5 is designed to transfer axial movement through the drug delivery device 1, for example for the purpose of delivering the drug 10. The piston rod 5 is axially displaceable in a dose delivery direction for delivering a dose of the drug 10. The dose delivery direction may be the distal direction with respect to the housing 2. Preferably, the piston rod 5 is prevented from being axially displaced in a dose setting direction by mechanical cooperation with further components of the drive mechanism. The dose setting direction may be the proximal direction with respect to the housing 2. Preferably, the piston rod 5 is prevented from being rotated with respect to the housing 2 when setting and when delivering a dose of the drug 10, for example, by mechanical cooperation with the housing 2. The drug delivery device 1 comprises a dose button 6 used for setting and/or dispensing a dose of the drug 10.

The drug delivery device 1 comprises cap 7. The cap 7 is configured to cover at least parts of the device 1. The cap 7 is configured to cover the dispensing end of the device 1. The cap 7 is adapted and arranged to cover a needle (not explicitly shown in the Figures) attached to the distal end of the device 1. Moreover, the cap 7 is adapted and arranged to cover at least a part of the drug retainer 3, 4. Preferably, the cap 7 covers the majority, such as 75% or more, of the drug retainer or the whole drug retainer 3, 4. The cap 7 can be connected, preferably releasably connected, to the drug retainer 3, 4. The cap 7 is connectable to the cartridge holder 3, for example. The cap 7 may be connectable to a proximal end section of the cartridge holder 3. The cap 7 may be connected to the cartridge holder 3 by a threaded connection or a snap-fit connection or a pin-groove cooperation. In the embodiment where the cartridge holder 3 is redundant, the cap 7 may be connectable directly to the cartridge 4. In an alternative embodiment, the cap 7 may be connected to the housing 2, in particular to a distal end section of the housing 2.

Figure 2:
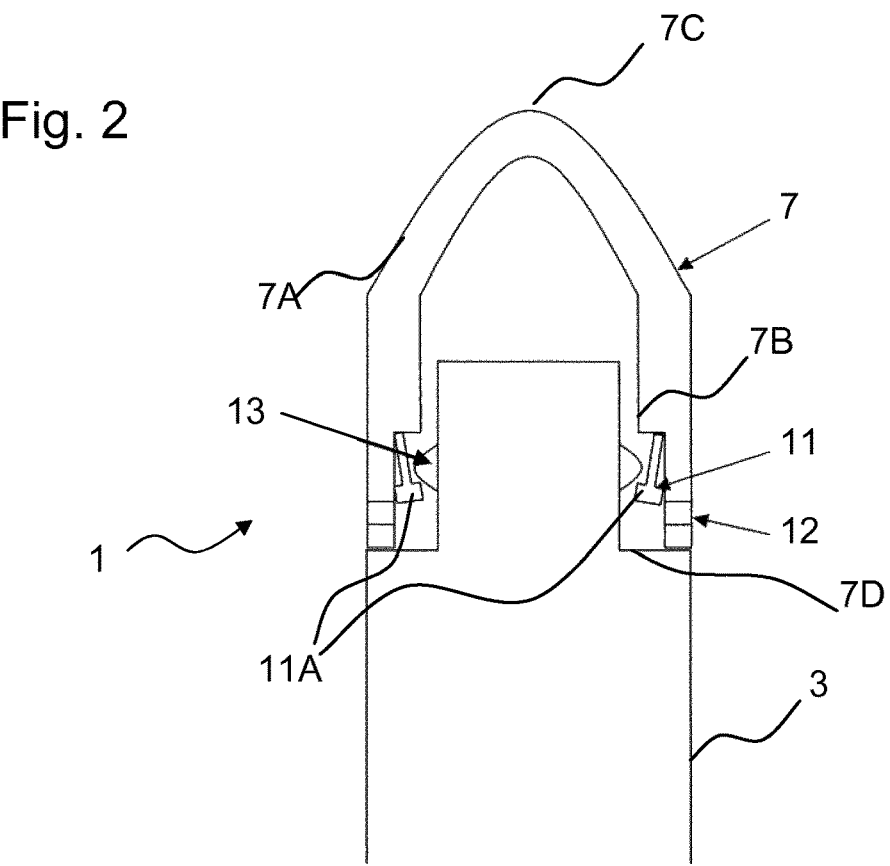
FIG. 2 schematically shows a sectional side view of a part of the drug delivery device of FIG. 1, FIG. 3 schematically shows a sectional side view of a part of the drug delivery device of FIG. 1.
Figure 3:
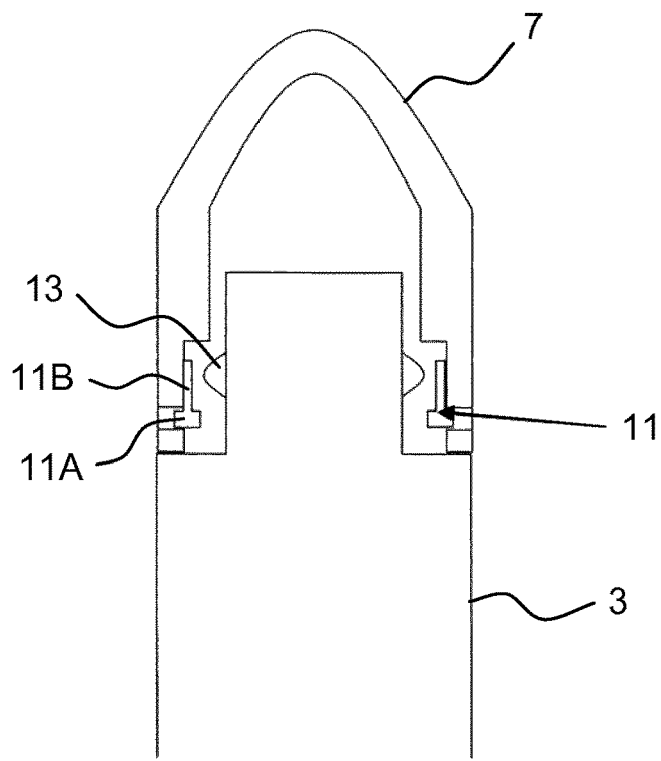

FIGS. 2 and 3 schematically show a sectional side view of a part of the drug delivery device 1 of FIG. 1.

The cap 7 comprises a main body 7A. The main body 7A is non-transparent. The main body 7A may be flexible. The main body 7A may be elastically deformable. The main body 7A comprises a closed end 7C. The closed end 7C is that end which is arranged closest to the dispensing end of the device 1 when the cap 7 is connected to the device 1. The cap 7 comprises an open end 7D. The open end 7D is configured to receive at least a part of the device 1, e.g. a part of the cartridge holder 3 or the complete cartridge holder 3. In particular, the open end 7D has a radial dimension suited to receive the cartridge holder 3 and/or the cartridge 4. The open end 7D is that end which is arranged furthest away from the dispensing end of the device 1 when the cap 7 is connected to the device 1.

The cap 7 comprises a display member 12. Alternatively, the cap 7 may comprise two, three or more display members 12. The display member 12 is configured to display information to the user. The display member 12 may be a window. The display member 12 may comprise an opening. The opening may be arranged in the surface of the main body 7A.

The cap 7 comprises an indication element 11. The indication element 11 is retained, preferably permanently retained, in the cap 7. In particular, the indication element 11 is not provided by the drug retainer 3, 4. Rather, the indication element 11 is provided by a component which is connectable to and moveable with respect to the drug retainer 3, 4, i.e. the cap 7.

The indication element 11 is moveably retained in the cap 7, in particular in the main body 7A. For example, the indication element 11 is moveable in the axial direction with respect to the main body 7A from a first position into a second position, which is described later on in more detail. The indication element 11 is arranged in the interior of the cap 7. The indication element 11 may be connected to the main body 7A, particularly via the inner surface thereof. In the depicted embodiment, the indication element 11 is connected to the main body 7A via a clamping action which is established between the main body 7A and the indication element 11. Other releasable connections, like a snap-fit connection, may also be applied for connecting the indication element 11 to the main body 7A. The connection is preferably strong enough to prevent accidental movement of the indication element 11 with respect to the main body 7A. Thus, the connection between the indication element 11 and the cap 7 is expediently a releasable stable connection which is stable until the connection is released deliberately.

The indication element 11 may be flexible. The indication element 11 is elastically deformable. The indication element 11 may comprise a plastic material, for example. The indication element 11 is arranged along the inner surface of the main body 7A. The indication element 11 is shaped ring-like or torus-like. In an alternative embodiment, the indication element 11 may comprise the shape of a flag or any shape which is conform with the described features of the indication element 11. The indication element 11 comprises a holding section 11B (see FIG. 2). The holding section 11B is configured to mechanically cooperate with the main body 7A, in particular the inner surface of the main body 7A, such that the indication element 11 is retained in the cap 7. For example, the indication element 11 is clamped to the cap 7 due to mechanical cooperation of the holding section 11B and the inner surface of the main body 7A.

The indication element 11 and, in particular the holding section 11B, mechanically cooperates with the inner wall of the main body 7A. The main body 7A, in particular the inner surface or wall of the main body 7A, comprises a blocking member 7B. The blocking member 7B may comprise a protrusion. The blocking member 7B may be arranged around the inner surface of the main body 7A. The blocking member 7B may comprise a flange. The blocking member 7B protrudes radially inwardly from the inner surface. Mechanical cooperation of the indication element 11, in particular the holding section 11B, and the blocking member 7B, prevents movement of the indication element 11 in the distal direction with respect to the main body 7A. In particular, due to mechanical cooperation of the blocking member 7B and the indication element 11, movement of the indication element 11 towards the closed end 7C of the cap 7 is limited. Due to mechanical cooperation of the blocking member 7B and the indication element 11 movement of the indication element 11 counter the direction in which the indication element 11 is moved when being moved from the first position into the second position, is prevented when the indication element 11 is in the first position.

The indication element 11 comprises a locking section 11A. The locking section 11A, in the depicted embodiment, comprises a smaller axial dimension than the holding section 11B. In other words, the holding section 11B is longer than the locking section 11A. The locking section 11A is arranged closer to the open end 7D of the cap 7 than the holding section 11B. The locking section 11A is arranged closer to the second position of the indication element 11 than the holding section 11B.

The locking section 11A may comprise a protrusion of the indication element 11. The locking section 11A may protrude in the radial direction with respect to the holding section 11B, preferably radially outwardly. The display member 12 is configured to receive the locking section 11A. The locking section 11A is configured to mechanically cooperate with the display member 12 for permanently locking the indication element 11 in the display member 12 when the indication element 11 is in the second position, which is described later on in detail.

The indication element 11 is moveable with respect to the main body 7A as mentioned above. The indication element 11 is moveable from the first position with respect to the main body 7A (see FIG. 2) into the second position with respect to the main body 7A (see FIG. 3). The first and the second positions are stable positions of the indication element 11. The first position may be a temporarily stable position. The first position may be temporarily stable due to mechanical cooperation of the holding section 11B and the main body 7A, in particular due to the holding section 11B being clamped into the main body 7A. From the first position, the indication element 11 may be moveable in the second position. The second position may be a permanently stable position. The first position may be permanently stable due to mechanical cooperation of the locking section 11A and the display 12, in particular due to the locking section 11A being locked in the display. The indication element 11 may not be moveable from the second position back in the first position. In the second position, the indication element 11 is expediently non-releasably connected to the main body 7A.

When the indication element 11 is in the first position, the indication element 11 cannot be viewed by the user. In particular, the indication element 11 is prevented from being viewed by the user by means of the main body 7A. The indication element 11 is completely hidden by means of the main body 7A. In the first position (see FIG. 2), the indication element 11 is biased. In particular, the indication element 11 is elastically deformed due to clamping the indication element 11 into the main body 7A. The indication element 11 is biased such that a force acts on the indication element 11 tending to move the indication element 11 in the radial outward direction with respect to the main body 7A. In the first position, the indication element 11 and, in particular, the holding section 11B, projects into the interior of the cap 7. The indication element 11 projects into the interior such that there is an angle between the holding section 11B and the inner surface of the main body 7A. The angle may be less than 90 degrees, preferably less than 45 degrees. The angle may be 15 degrees or more. In the first position, the indication element 11 and, in particular the holding section 11B, may abut the blocking member 7B of the main body 7A. Accordingly, the first position may be the most distal position of the indication element 11 with respect to the main body 7A. The position may be temporarily stable such that the indication element 11 is moveable from the first position into the second position.

In the second position (see FIG. 3), the indication element 11 is less biased than in the first position. In particular, the angle between the holding section 11B and the inner surface of the main body 7A may be less than 10 degrees, preferably 0 degrees when the indication element 11 is in the second position. When the indication element 11 is in the second position, there is no angle between the holding section 11B and the inner surface of the main body 7A. The holding section 11B may abut the inner surface of the main body 7A when the indication element 11 is in the second position. The second position is a permanently stable position as described above. In the second position, the indication element 11 and, in particular, the locking section 11A is locked in the display member 12. In particular, the locking section 11A mechanically cooperates with the display member 12 such that the indication element 11 is received in the display member 12 and permanently locked in the second position. In the second position at least a part of the indication member 11, in particular the locking section 11A, can be viewed by the user. In particular, the locking section 11A can be viewed through the display member 12. In the second position, the indication element 11 and, in particular the holding section 11B, is prevented from abutting the blocking member 7B of the main body 7A. Accordingly, the second position may be the most proximal position of the indication element 11 with respect to the main body 7A.

The device 1 comprises an interaction member 13. Alternatively, the device 13 may comprise two, three or more interaction members 13. The interaction member 13 may be part of a component of the device 1. The interaction member 13 may be provided by the drug retainer 3, 4. For example, the interaction member 13 may be part of the cartridge holder 3. Alternatively, in the embodiment where the cartridge holder 3 is redundant, the interaction member 13 may be part of the cartridge 4. The interaction member 13 is configured for moving the indication element 11 from the first position into the second position, which is described later on in detail.

The interaction member 13 may be a protrusion. The interaction member 13 may comprise a cam. The interaction member 13 is adapted and arranged to interact with the indication element 11. When the interaction member 13 mechanically cooperates with the indication element 11, the indication element 11 is moved from the first position to the second position. The axial position of the interaction member 13 with respect to the housing 2 depends on the axial position of the indication element 11 with respect to the housing 2 when the cap 7 is connected to the device 1. The interaction member 13 comprises an axial position with respect to the housing 2 such that the indication element 11 passes along the interaction member 13 when the cap 7 is moved with respect to the device 1 for connecting or disconnecting the cap 7 to or from the device 1. The interaction member 13 may be arranged in the distal end section of the device 1, for example. Alternatively, the interaction member 13 can be arranged in the middle section or in the proximal end section of the device 1 depending on the axial position of the indication element 11 as described above. The axial position of the interaction member 13 may be more distal than the axial position of the locking section 11A of the indication element 11.

The cap 7 and, in particular, the indication element 11 and the display member 12 are configured for displaying an information to the user. The information may indicate the state of use of the device 1. The information may indicate whether the cap 7 has been removed from the device 1 for the first time or not. Accordingly, with the term that the information indicates a state of use, it is not necessarily meant that the information indicates whether a dose of drug has already been dispensed from the device 1. Rather, the information may indicate whether the user has removed the cap 7 from the device 1 at least once and, thus, has reduced the sterility of the device 1 as compared to the state as supplied by the manufacturer.

For displaying this information, the indication element 11 has a colour which is different from a colour of the cap. The indication element 11 may have a blue colour, for example, and the cap 7 may have a white colour, for example. The information provided to the user changes when the indication element 11 is moved from the first position into the second position. This is described in the following:

When the device is supplied from the manufacturer, the indication element 11 is in the first position. When assembling the device 1 during manufacture, the cap 7 is guided along the interaction member 13 for connecting the cap 7 to the device 1 under sterile conditions. Thereby, mechanical cooperation between the interaction member 13 and the locking section 11A is prevented due to the flexibility of the main body 7A and, in particular, the flexibility of the indication element 11 clamped into the main body 7A.

Accordingly, when the device 1 is provided from the manufacturer, the cap 7 is connected to the device 1. When the device 1 is provided from the manufacturer to the user, the device 1 is new. Accordingly, it has never been used before and the cap 7 was not yet removed from the device 1 for the first time. When the device 1 is provided from the manufacturer, the indication element 11 is positioned in the first position, as described above (see FIG. 2). Accordingly, the user cannot see the locking section 11A through the display member 12. Rather, the user can only see the cap 7 having the white colour, for example. The white colour indicates that the device 1 has not yet been used and, in particular, that the cap 7 has not yet been removed from the device 1 for the first time.

For being able to use the device 1 for the first time, the user must remove the cap 7 from the device 1. When the user moves the cap 7 with respect to the housing 2 for removing the cap 7 from the device 1, the indication element 11 is moved along the cartridge holder 3 (and/or the cartridge 4) in the distal direction with respect to the housing 2 and with respect to the interaction member 13. In particular, the indication element 11 is passed along the interaction member 13. Thereby, the interaction member 13 mechanically cooperates with the locking section 11A. This is possible as the indication element 11 projects into the interior of the cap 7 when the indication element 11 is in the first position, as described above. Hence, the interaction member 13 and the locking section 11A radially overlap when the indication element 11 is in the first position. The interaction member 13 urges the indication element 11 distally as well as in the radial outward direction with respect to the main body 7A and into the second position. When the indication element 11 is moved into the second position, the information provided by the cap 7 changes. In particular, upon movement of the indication element 11 into the second position, the locking section 11A at least partially relaxes radially outwardly into the display member 12, thereby engaging the display member 12. Thus, the locking section 11A becomes visible through the display member 12. Thus, the user can see the, for example blue, colour of the indication element 11 indicating that the device 1 is in use and, in particular, that the cap 7 was removed at least once from the device 1, thereby having reduced the sterility of the device 1.

In the second position, the indication element 11 is permanently locked against movement due to mechanical cooperation with the display member 12. Accordingly, the indication element 11 cannot be moved from the second position back into the first position. When the indication element 11 is in the second position, the indication element 11 no longer projects into the cap 7 such that it can mechanically cooperate with the interaction member 13. In particular, further mechanical cooperation between the indication element 11 and the interaction member 13 is prevented as there is a radial distance between the locking section 11A and the interaction member 13 when the indication element 11 is in the second position (see FIG. 3).

As soon as the cap 7 is removed from the device 1, the user can use the device 1 for setting and dispensing a dose of the drug 10. Afterwards, the user can move the cap 7 in the proximal direction with respect to the housing 2 for re-connecting the cap 7 to the device. Thereby, mechanical cooperation between the interaction member 13 and the indication element 11 is prevented due to the radial distance described above. Accordingly, the user can easily slide the cap 7 over the device 1 for connecting the cap 7 to the device 1, the indication element 11 being permanently locked in the second position and the cap 7 thus permanently providing the information that that the cap 7 was removed at least once from the device 1. When the cap 7 is removed from the device 1 for the second time and for subsequent times, the indicated information does not change.

Of course, features of different embodiments described herein can be combined with one another to form further embodiments which were not described above.

The invention claimed is:

1. A drug delivery device comprising;
   a cap comprising
      a main body comprising a closed end, wherein the closed end is a distal end of the main body, and
      an indication element connected to an inner surface of the main body, and
   a drug retainer comprising an interaction member adapted and arranged to interact with the indication element to move the indication element from a first position to a second position with respect to the main body,
   wherein an information indicated to a user by the cap is changed when the indication element is moved from the first position into the second position,
   wherein, when the indication element is positioned in the first position, the indication element is prevented from being viewed by a user, and
   wherein, when the indication element is positioned in the second position, the indication element is visible to the user.

2. The drug delivery device according to claim 1, comprising at least one display member configured to display the information to the user.

3. The drug delivery device according to claim 1, wherein the indication element is biased when the indication element is positioned in the first position, and wherein, when the indication element is in the second position, the bias is reduced as compared to the bias in the first position.

4. The drug delivery device according to claim 1, wherein the indication element comprises a locking section, wherein the locking section is adapted and arranged such that the indication element is locked in the second position against movement back into the first position due to mechanical cooperation of the locking section and the main body.

5. The drug delivery device according to claim 4, wherein the indication element is locked in the second position due to mechanical cooperation of the locking section and a display member.

6. The drug delivery device according to claim 5, wherein the locking section comprises a protrusion, and wherein the display member comprises an opening.

7. The drug delivery device according to claim 1, wherein the indication element comprises a holding section, and wherein the holding section is configured for retaining the indication element in the main body.

8. The drug delivery device according to claim 1, wherein the cap comprises a blocking member, wherein, when the indication element is in the first position, the blocking member is configured to prevent a movement of the indication element counter to the direction in which the indication element is moved when being moved from the first position into the second position by mechanical cooperation with the indication element.

9. The drug delivery device according to claim 1, wherein the indication element is shaped ring-like.

10. The drug delivery device according to claim 1, wherein the indication element comprises a colour which is different from a colour of the cap.

11. The drug delivery device according to claim 1, wherein the interaction member comprises a cam.

12. The drug delivery device according to claim 1, wherein the cap is connected to a component of the drug delivery device, and wherein the interaction member is arranged such that the indication element passes along the interaction member when the cap is removed from the drug delivery device and such that the interaction member mechanically cooperates with the indication element for moving the indication element from the first position into the second position.

13. A drug delivery device comprising:
   a cap comprising:
      a main body comprising a closed end, and
      an indication element connected to an inner surface of the main body;
   a drug retainer; and
   an interaction member, wherein the interaction member is part of the drug retainer,
   wherein the indication element is moveable from a first position to a second position with respect to the main body,
   wherein the interaction member is adapted and arranged to interact with the indication element to move the indication element from the first position to the second position,
   wherein an information indicated to a user by the cap is changed when the indication element is moved from the first position into the second position,
   wherein, when the indication element is positioned in the first position, the indication element is prevented from being viewed by a user, and
   wherein, when the indication element is positioned in the second position, the indication element is visible to the user.

* * * * *

UNITED STATES PATENT AND TRADEMARK OFFICE
CERTIFICATE OF CORRECTION

| | |
|---|---|
| PATENT NO. | : 10,130,778 B2 |
| APPLICATION NO. | : 14/421356 |
| DATED | : November 20, 2018 |
| INVENTOR(S) | : Jugl et al. |

Page 1 of 1

It is certified that error appears in the above-identified patent and that said Letters Patent is hereby corrected as shown below:

In the Claims

Column 13, Line 22, Claim 1, delete "comprising;" and insert -- comprising: --

Signed and Sealed this
Twelfth Day of March, 2019

Andrei Iancu
*Director of the United States Patent and Trademark Office*